(12) United States Patent
Savin-Poncet et al.

(10) Patent No.: US 7,393,877 B2
(45) Date of Patent: Jul. 1, 2008

(54) PROCESS FOR THE CONVERSION OF A SYNTHESIS GAS TO HYDROCARBONS IN THE PRESENCE OF BETA-SIC AND EFFLUENT FROM THIS PROCESS

(75) Inventors: Sabine Savin-Poncet, Buros (FR); Marc-Jacques Ledoux, Strasbourg (FR); Cuong Pham-Huu, Saverne (FR); Jacques Bousquet, Irigny (FR); Behrang Madani, Strasbourg (FR)

(73) Assignees: Total France, Puteaux (FR); Total S.A., Courbevoie (FR)

( * ) Notice: Subject to any disclaimer, the term of this patent is extended or adjusted under 35 U.S.C. 154(b) by 77 days.

(21) Appl. No.: 11/411,085

(22) Filed: Apr. 26, 2006

(65) Prior Publication Data

US 2006/0194888 A1    Aug. 31, 2006

Related U.S. Application Data

(63) Continuation of application No. 11/027,706, filed on Jan. 3, 2005, now abandoned.

(30) Foreign Application Priority Data

Dec. 31, 2003   (FR)   .................... 03 15622

(51) Int. Cl.
C07C 27/00   (2006.01)
(52) U.S. Cl. .................. 518/721; 518/700; 518/713; 518/714; 518/715; 518/716; 518/717; 518/719
(58) Field of Classification Search ........... 518/700, 518/713–717, 719, 721
See application file for complete search history.

(56) References Cited

U.S. PATENT DOCUMENTS

| | | | |
|---|---|---|---|
| 4,260,521 A | 4/1981 | Kostka |
| 4,914,070 A | 4/1990 | Ledoux |
| 5,196,389 A | 3/1993 | Dubots |
| 5,217,930 A | 6/1993 | Dubots |
| 5,427,761 A | 6/1995 | Grindatto |
| 5,449,654 A | 9/1995 | Prin |
| 5,460,759 A | 10/1995 | Dubots |
| 5,585,316 A | 12/1996 | Nay |
| 5,648,312 A | 7/1997 | Rivas |
| 5,677,257 A | 10/1997 | Rivas |
| 5,710,093 A | 1/1998 | Rivas |
| 6,121,190 A | 9/2000 | Zennaro et al. |
| 6,217,841 B1 | 4/2001 | Grindatto |
| 6,251,819 B1 | 6/2001 | Prin |
| 6,296,757 B1 | 10/2001 | Wittenbrink et al. |
| 6,361,861 B2 | 3/2002 | Gao |
| 6,921,778 B2 | 7/2005 | Minkkinen |

| | | |
|---|---|---|
| 2005/0171218 A1 | 8/2005 | Savin-Poncet |

FOREIGN PATENT DOCUMENTS

| | | |
|---|---|---|
| CN | 1351954 | 6/2002 |
| EP | 0 440 569 A2 | 8/1991 |
| EP | 0 511 919 A1 | 11/1992 |
| EP | 0 543 751 A1 | 5/1993 |
| EP | 0 543 752 A1 | 5/1993 |
| EP | 0 857 513 A1 | 8/1998 |
| EP | 1 284 281 A1 | 2/2003 |
| EP | 1 338 335 A1 | 8/2003 |
| FR | 2 062 615 | 6/1971 |
| FR | 2 832 415 A1 | 5/2003 |
| FR | 2 864 532 A1 | 7/2005 |
| WO | WO 97/14768 A1 | 4/1997 |
| WO | WO 97/14769 A1 | 4/1997 |
| WO | WO 98/05740 A1 | 2/1998 |
| WO | WO 98/34998 A1 | 8/1998 |
| WO | WO 98/34999 A1 | 8/1998 |
| WO | WO 98/38147 A1 | 9/1998 |
| WO | WO 99/01218 A1 | 1/1999 |
| WO | WO 99/13028 A1 | 3/1999 |
| WO | WO 99/13029 A1 | 3/1999 |
| WO | WO 99/13030 A1 | 3/1999 |
| WO | WO 99/13031 A1 | 3/1999 |
| WO | WO 99/21943 A1 | 5/1999 |
| WO | WO 00/11116 A1 | 3/2000 |
| WO | WO 00/11117 A1 | 3/2000 |
| WO | WO 00/20534 A1 | 4/2000 |

(Continued)

OTHER PUBLICATIONS

Bradford and Vannice, $CO_2$ reforming of $CH_4$, Catal. Rev.—Sci. Eng., 41(1), pp. 1-42 (1999).

(Continued)

Primary Examiner—Jafar Parsa
(74) Attorney, Agent, or Firm—Rothwell, Figg, Ernst & Manbeck, P.C.

(57) ABSTRACT

In a process for the conversion of carbon monoxide to $C_2^+$ hydrocarbons in the presence of hydrogen and of a catalyst comprising a metal and a support comprising silicon carbide, the support comprises more than 50% by weight of silicon carbide in the beta form. A process for the conversion of carbon monoxide to $C_2^+$ hydrocarbons in the presence of hydrogen and of a catalyst the effluent thus obtained are also disclosed.

28 Claims, 8 Drawing Sheets

FOREIGN PATENT DOCUMENTS

| | | |
|---|---|---|
| WO | WO 00/20535 A1 | 4/2000 |
| WO | WO 00/60029 A1 | 10/2000 |
| WO | WO 00/61707 A1 | 10/2000 |
| WO | WO 01/12323 A2 | 2/2001 |
| WO | WO 01/16259 A1 | 3/2001 |
| WO | WO 01/49812 A1 | 7/2001 |
| WO | WO 01/54812 A1 | 8/2001 |
| WO | WO 01/59034 A2 | 8/2001 |
| WO | WO 01/62875 A2 | 8/2001 |
| WO | WO 01/83406 A2 | 11/2001 |
| WO | WO 01/83641 A2 | 11/2001 |
| WO | WO 01/83647 A2 | 11/2001 |
| WO | WO 01/83648 A2 | 11/2001 |
| WO | WO 02/02490 A2 | 1/2002 |
| WO | WO 02/070628 A2 | 9/2002 |
| WO | WO 03/000398 A2 | 1/2003 |
| WO | WO 03/004588 A2 | 1/2003 |

OTHER PUBLICATIONS

R. Moene, *Application of chemical vapour deposition in catalyst design, development of high surface area silicon carbide as catalyst support*, Thesis Delft University of Technology (1995); ISBN 90-407-1109-7, pp. 1-201.

Choudary et al., *Energy efficient methane-to-syngas conversion with low $H_2/CO$ ratio by simultaneous catalytic reactions of methane with carbon dioxide and oxygen*, Catalysis Letters 32, pp. 391-396 (1995).

Choudary & Mamman, *Energy efficient conversion of methane to syngas over NiO-MgO solid solution*, Applied Energy 66, pp. 161-175 (2000).

Ruckenstein & Hang Hu, *Combination of $CO_2$ reforming and partial oxidation of methane over NiO/MgO solid solution catalysts*, Ind. Eng. Chem. Res. 37, pp. 1744-1747 (1998).

O'Connor & Ross, *The effect of $O_2$ addition on the carbon dioxide reforming of methane over $Pt/ZrO_2$ catalysts*, Catalysis Today 46, pp. 203-210 (1998).

Quincoces et al., *Role of Mo in $CO_2$ reforming of $CH_4$ over Mo promoted $Ni/Al_2O_3$ catalysts*, Materials Letters 56, pp. 698-704 (2002).

Tomishige et al., *Catalyst development for direct heat supply from combustion to reforming in methane reforming with $CO_2$ and $O_2$*, Applied Catalysis A: General 244, pp. 71-82 (2003).

Mo et al., *Reforming of methane with oxygen and carbon dioxide to produce syngas over a novel $Pt/CoAl_2O_4/Al_2O_3$ catalyst*, Journal of Molecular Catalysis A: Chemical 193, pp. 177-184 (2003).

Yan et al., *Activation of methane to syngas over a $Ni/TiO_2$ catalyst*, Applied Catalysis A: General 239, pp. 43-58 (2003).

Seok et al., *Mn promoted $Ni/Al_2O_3$ catalysts for stable carbon dioxide reforming of methane*, Journal of Catalysis 209, pp. 6-15 (2002).

Kameyama et al., "Preparation of ultrafine Fe-Si-C powders in a radio-frequency thermal plasma and their catalytic properties", Journal of Materials Science, vol. 28, (1993), 4630-4636.

PROCESS FOR THE CONVERSION OF A SYNTHESIS GAS TO HYDROCARBONS IN THE PRESENCE OF BETA-SIC AND EFFLUENT FROM THIS PROCESS

TECHNICAL FIELD

The present invention relates to a process for the conversion of synthesis gas to $C_2^+$ hydrocarbons by Fischer-Tropsch synthesis. It also relates to a Fischer-Tropsch synthesis process which produces an effluent exhibiting a specific distribution of the liquid fraction, and to this effluent.

PRIOR ART

Numerous documents are known which describe the Fischer-Tropsch (FT) synthesis using metal catalysts supported on various catalytic supports.

The documents WO-A-01/12323 and WO-A-01/54812 (Battelle) mention carbides generically as support or as interfacial layer for catalytic systems for the FT synthesis. There is no mention of the type of carbide which may be used.

U.S. Pat. Nos. 5,648,312, 5,677,257 and 5,710,093 (Intevep) disclose a specific catalytic support suitable for the FT synthesis (capable of being employed in a fixed bed, an ebullating bed or as a slurry). The catalytic entity in these documents is a metal from Group IVB or VIII, or a mixture, in particular zirconium and cobalt.

This support is obtained in particular by the formation of a suspension of silica and of silicon carbide in a basic solution, the formation of drops and then their separation as spheres, and then the transfer of the spheres into an acidic solution to result in a catalytic support comprising a substantially homogeneous mixture of silica and of SiC. Processes for the synthesis of hydrocarbons from synthesis gas use this catalytic support, which is a homogeneous mixture of particles of silica and of SiC, in an amount of 10 to 50% of the support, the support having a specific surface of at least approximately 30 $m^2/g$ (preferably of greater than 40 $m^2/g$), mean pore diameters of at least approximately 150 Å and a particle size of at least 0.1 mm. From the synthesis, the SiC necessarily has the alpha form. In these documents, the binder of this SiC being the silica. The specific surface is conferred by the silica binder rather than by the form of the SiC; the latter is used in fact more as a heat sink rather than as a support as such.

The presence of silica and/or of alumina as binder can have a negative effect on the thermal conductivity of the support. In addition, this binder, as support, additionally exhibits the disadvantage of reacting with the catalytic entity, thus resulting in a loss in the activity over time.

SUMMARY OF THE INVENTION

The invention provides a novel FT synthesis process using a novel catalytic support comprising β-SiC. A support is thus obtained which, in comparison with the supports of the prior art, is particularly suitable for the exothermic reaction of the FT synthesis.

Thus, the invention provides a process for the conversion of carbon monoxide to $C_2^+$ hydrocarbons in the presence of hydrogen and of a catalyst comprising a metal and a support comprising silicon carbide, characterized in that the support comprises more than 50% by weight of silicon carbide in the beta form.

A further subject-matter of the invention is a process for the conversion of carbon monoxide to $C_2^+$ hydrocarbons in the presence of hydrogen and of a catalyst, characterized in that the hydrocarbon effluent comprises more than 70 mol % of a mixture comprising from 50 to 90 mol % of $C_6$ to $C_{12}$ hydrocarbons and from 10 to 50 mol % of $C_{13}$ to $C_{24}$ hydrocarbons.

A further subject-matter of the invention is a $C_2^+$ hydrocarbon effluent comprising hydrocarbons, methane and $CO_2$ which comprises more than 70 mol % of a mixture comprising from 50 to 90 mol % of $C_6$ to $C_{12}$ hydrocarbons and from 10 to 50 mol % of $C_{13}$ to $C_{24}$ hydrocarbons.

BRIEF DESCRIPTION OF THE DRAWINGS

The invention is described in more detail with reference to the appended drawings, in which.

DETAILED DESCRIPTION OF EMBODIMENTS OF THE INVENTION

Figure 1A:
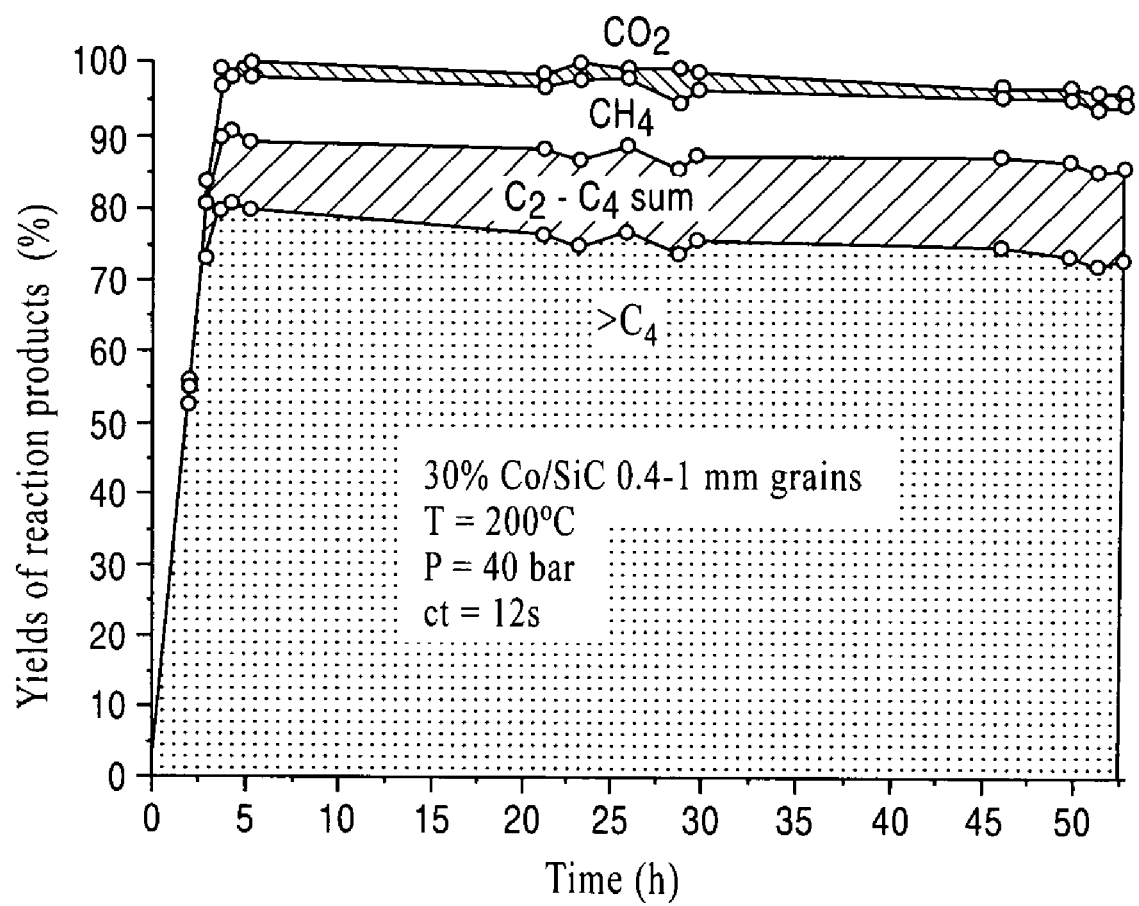
FIG. 1A gives the results of the yields of the various fractions as a function of the time under flow for a first embodiment.

The beta-SiC is prepared by a gas/solid reaction between intimately mixed (without liquid) SiO vapour and solid carbon. For further details with regard to the β-SiC, reference may be made to the following patent applications and patents, incorporated by reference in the present application: EP-A-0 313 480, EP-A-0 440 569, U.S. Pat. No. 5,217,930, EP-A-0 511 919, EP-A-0 543 751 and EP-A-0 543 752. In comparison with the alpha form, the β-SiC is characterized in particular in that it exists in the pure state without binder. The crystals are of face-centred cubic type. In general, the specific surface of the β-SiC is between 5 and 40 $m^2/g$ and preferably between 10 and 25 $m^2/g$.

The β-SiC can be prepared in the form of a powder, grains, extrudates (without binder), foam, monolith, and the like. The size of the SiC can vary according to the type of process employed (fixed bed, ebullating bed, slurry bed). It is thus possible, according to one alternative form, to use a size of between 0.1 and 20 mm, preferably between 1 and 15 mm. According to another alternative form, it is possible to use a size of between 1 and 200 μm, preferably between 5 and 150 μm.

This β-SiC has very good mechanical properties. Because of its very good thermal conductivity, generally much greater than that of metal oxides, hot spots are limited to the surface of the catalyst. The selectivity is thus improved.

According to one embodiment, the support of the catalyst comprises from 50 to 100% by weight of beta silicon carbide in the particulate state and preferably 100% of the said silicon carbide.

Use may conventionally be made, as main metal catalyst, of metals from Group VIII, for example in particular cobalt, iron or ruthenium, cobalt being particularly preferred. Use may also be made conventionally, at the same time, of a promoter. Mention may be made, among the promoters, of another metal from Group VIII or also of metals chosen from the group consisting of Zr, K, Na, Mn, Sr, Cu, Cr, W, Re, Pt, Ir, Rh, Pd, Ru, Ta, V, Mo and their mixtures. Mo is preferred.

The content of main metal, in particular cobalt, is conventionally greater than 5%, typically between 10 and 50%, of the final weight of the catalyst, in particular between 20 and 35% by weight. The content of promoter, in particular molybdenum, is conventionally between 0.1 and 15% of the final weight of the catalyst, in particular between 2 and 10% by weight. A primary metal/promoter ratio by weight is conventionally from 10:1 to 3:1.

The catalytic metal is deposited conventionally. For example, use may be made of the impregnation of the pore volume by a salt of the metal, for example cobalt nitrate. Use may also be made of the evaporated drop (also known as egg shell) method, by dropwise addition of a metal salt solution at ambient temperature to a support at high temperature, resulting in deposition essentially at the surface, for example a cobalt nitrate solution under air to a support at 200° C.

The catalytic bed can be fixed, ebullating or as a slurry. A fixed bed will be preferred.

The Fischer-Tropsch synthesis reaction is generally carried out under the following operating conditions:
 total pressure: 10 to 100, preferably 20 to 50, atmospheres;
 reaction temperature: 160 to 250° C., preferably 180 to 220° C.;
 GHSV varying from 150 to 5000 $h^{-1}$, preferably from 200 to 1000 $h^{-1}$;
 $H_2$/CO ratio of the starting synthesis gas of between 1.2 and 2.8, preferably between 1.7 and 2.3.

The present invention also relates to an FT synthesis process which produces a hydrocarbon effluent which comprises at least 70 mol % of $C_5$ to $C_{25}$ hydrocarbons and in which the distribution is centred around relatively light hydrocarbons, approximately from $C_7$ to $C_{10}$. This type of distribution is not conventional, in particular for a process carried out in a fixed bed.

According to one embodiment, the hydrocarbon effluent comprises more than 70 mol % of a mixture comprising from 50 to 90 mol % of $C_6$ to $C_{12}$ hydrocarbons and from 10 to 50 mol % of $C_{13}$ to $C_{24}$ hydrocarbons.

According to one embodiment, the hydrocarbon effluent comprises at most 10 mol % of branched hydrocarbons and olefins and/or less than 2 mol % of $C_1$ to $C_{20}$ alcohol.

According to one embodiment, in the hydrocarbon effluent, the content of methane and of $CO_2$ is less than 20 mol %.

Another subject-matter of the invention is this specific FT synthesis effluent.

In the patent application, the ratios are molar, unless otherwise mentioned.

The following examples illustrate the invention without limiting it.

EXAMPLE 1

Fischer-Tropsch Synthesis Over a Catalyst Based on Cobalt Supported on β-SiC.

In this example, the support based on β-SiC, in the form of grains with a diameter of between 0.4 and 1 mm, is impregnated by the pore volume method with an aqueous solution comprising the cobalt salt in the nitrate form. The weight of the precursor salt is calculated in order to have a final cobalt charge of 30% by weight with respect to the weight of catalyst after calcination and reduction. The impregnated product is subsequently dried under air at 100° C. for 2 h and then calcined under air at 350° C. for 2 h, in order to convert the precursor salt to its corresponding oxide. The product after calcination is reduced under a stream of hydrogen at 400° C. for 2 h in order to obtain the metallic form of the active phase.

The Fischer-Tropsch synthesis reaction is carried out under the following conditions:
 total pressure: 40 atmospheres
 reaction temperature: 200° C.
 reactants/catalyst contact time: 12 sec.
 $H_2$/CO molar ratio of 2.

Figure 1B:
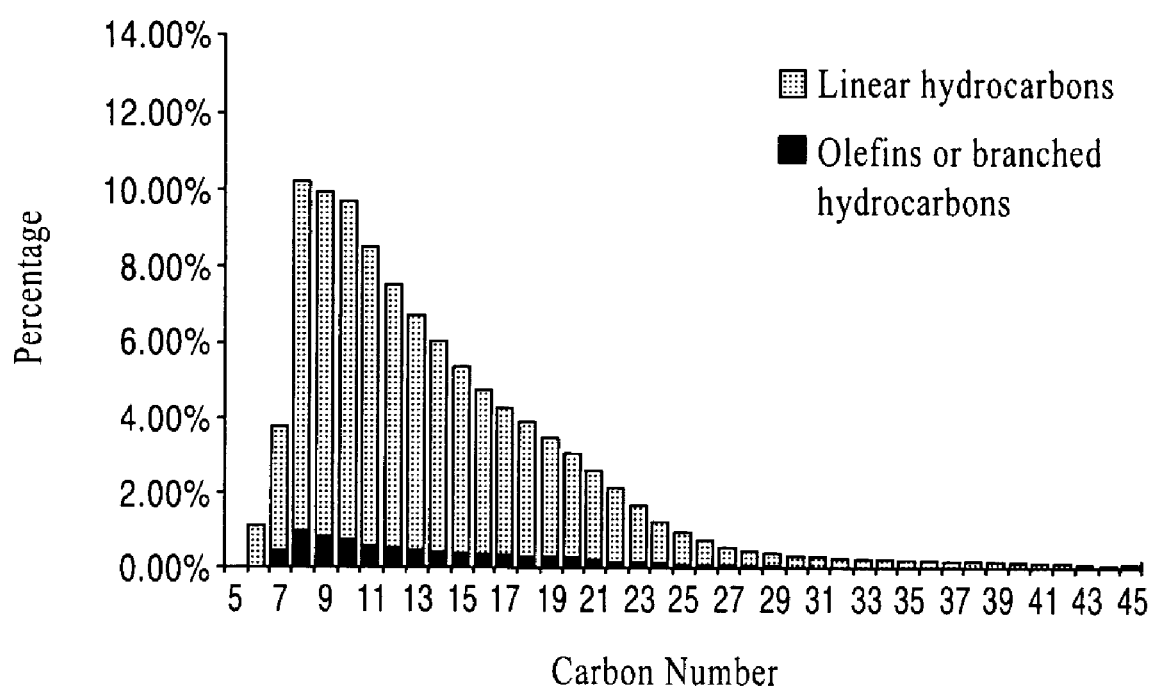
FIG. 1B gives the distribution of the hydrocarbons within the liquid fraction for this first embodiment.

The results obtained, expressed in terms of yields of the various fractions, are presented in FIG. 1A as a function of the time under flow. As may be observed, the catalyst based on Co/β-SiC exhibits a very good activity for the formation of liquid hydrocarbons from the CO/$H_2$ mixture. The distribution of the hydrocarbons within the liquid fraction ($C_4^+$) is presented in FIG. 1B. From the results obtained, the liquid fraction is essentially composed of paraffin hydrocarbons ranging from $C_6$ to $C_{25}$, i.e. >90%; in particular, a noteworthy distribution of light hydrocarbons of the petrol fraction is recorded, with levels of greater than 6% for the $C_7$, $C_8$, $C_9$, $C_{10}$, $C_{11}$, $C_{12}$ and $C_{13}$ hydrocarbons and levels of greater than 8% for the $C_8$, $C_9$, $C_{10}$ and $C_{11}$ hydrocarbons, whereas the concentration of the olefinic hydrocarbons remains low (less than 1% on average).

EXAMPLE 2

Influence of Molybdenum as Promoter on the Fischer-Tropsch Synthesis Activity of a Catalyst Based on Cobalt Supported on β-SiC.

In this example, the consequences on the performance of the Co/β-SiC catalyst in the presence of a promoter which is molybdenum are recorded. In this example, the support based on β-SiC, in the form of grains with a diameter of between 0.4 and 1 mm, is impregnated by the pore volume method with an aqueous solution comprising the cobalt salt in the nitrate form and an aqueous solution comprising an ammonium molybdate tetrahydrate. The weight of the precursor salt is calculated in order to have a final cobalt charge of 30% by weight with respect to the weight of the catalyst and a molybdenum charge of 5% by weight with respect to the weight of the catalyst, after calcination and reduction. The preparation of the catalyst is the same as in Example 1.

The Fischer-Tropsch synthesis reaction is carried out under the same conditions as in Example 1.

Figure 2A:
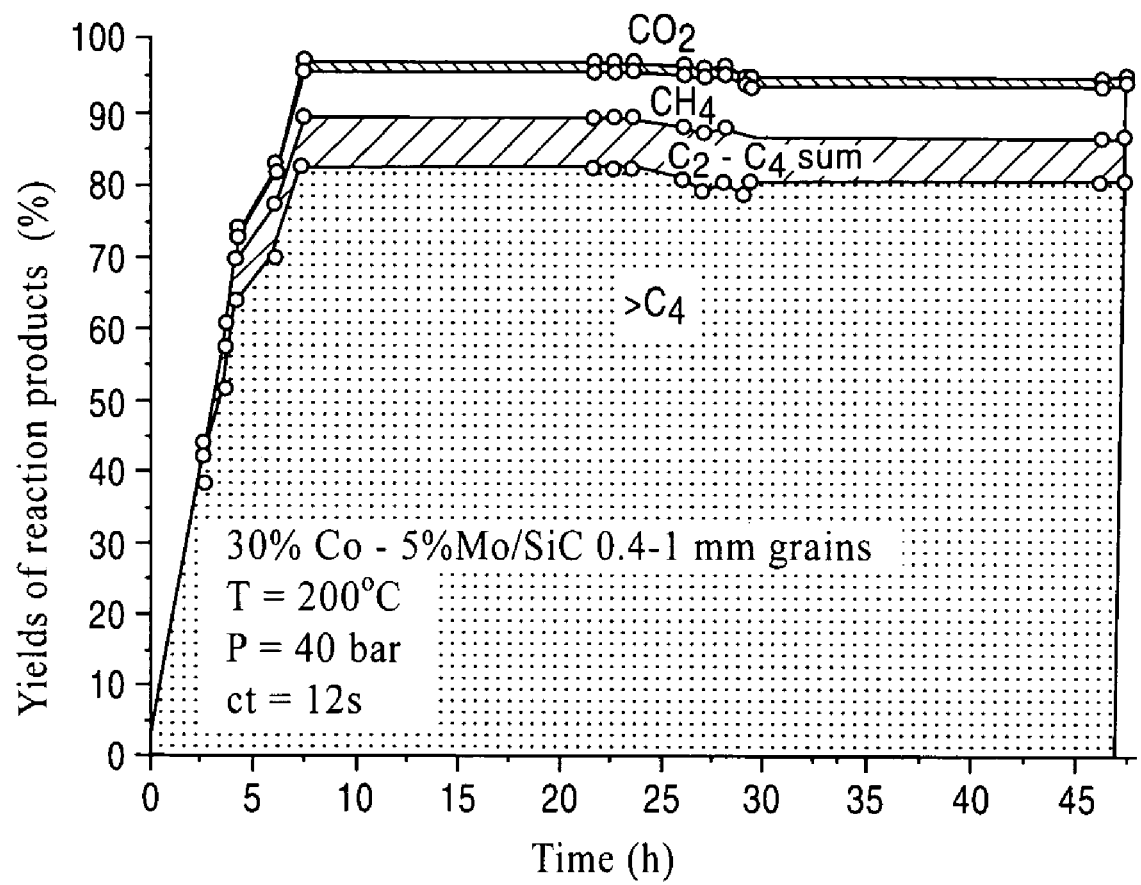
FIG. 2A gives the results of the yields of the various fractions as a function of the time under flow for a second embodiment.
Figure 2B:
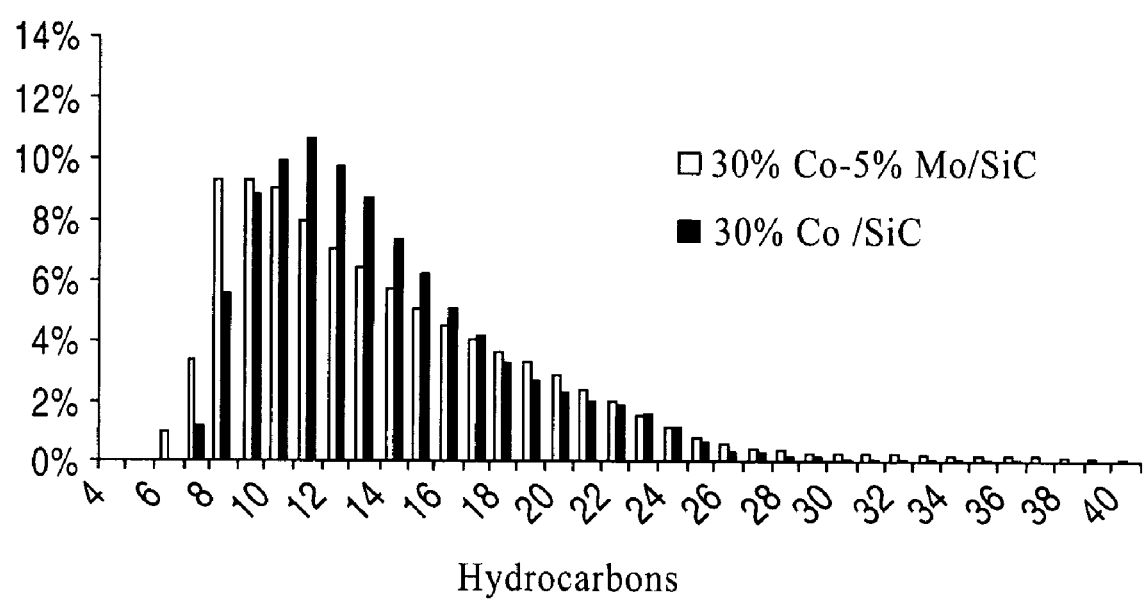
FIG. 2B gives the distribution of the hydrocarbons within the liquid fraction for the second embodiment.
Figure 3A:
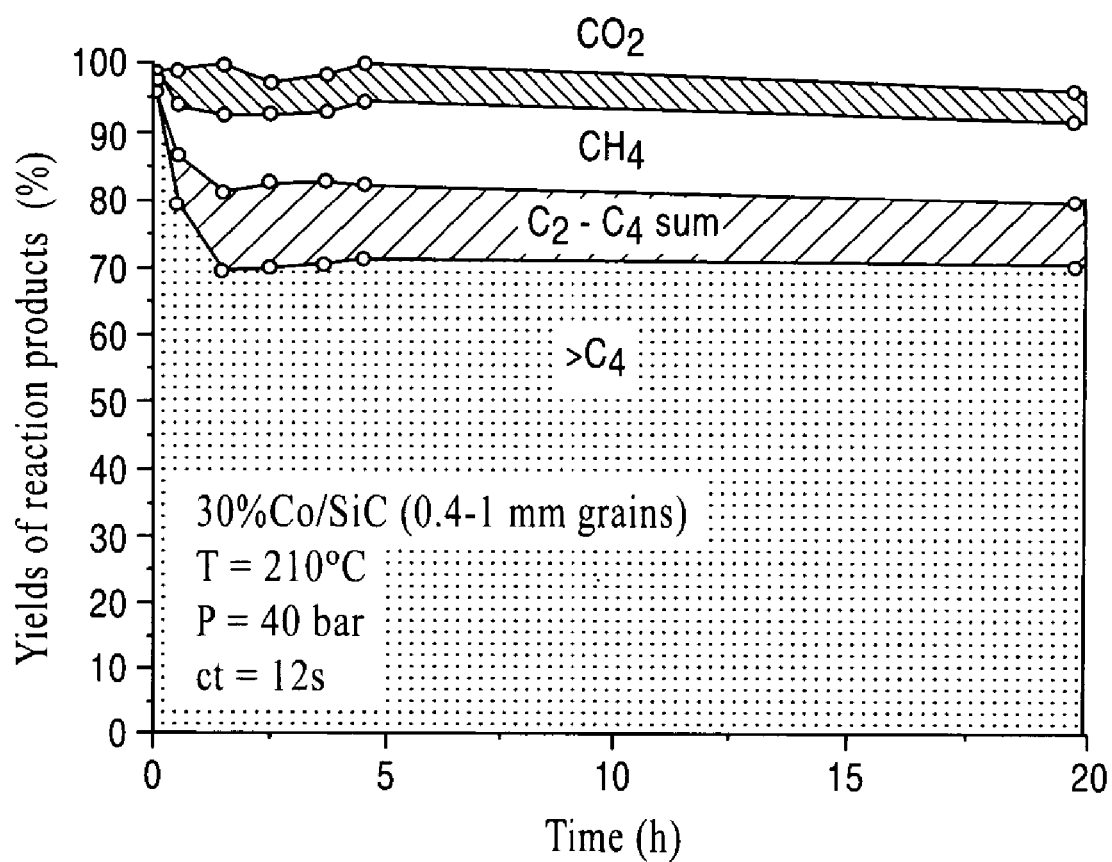
FIGS. 3A and 3B give the results of the yields of the various fractions as a function of the time under flow for third and fourth embodiments.
Figure 3B:
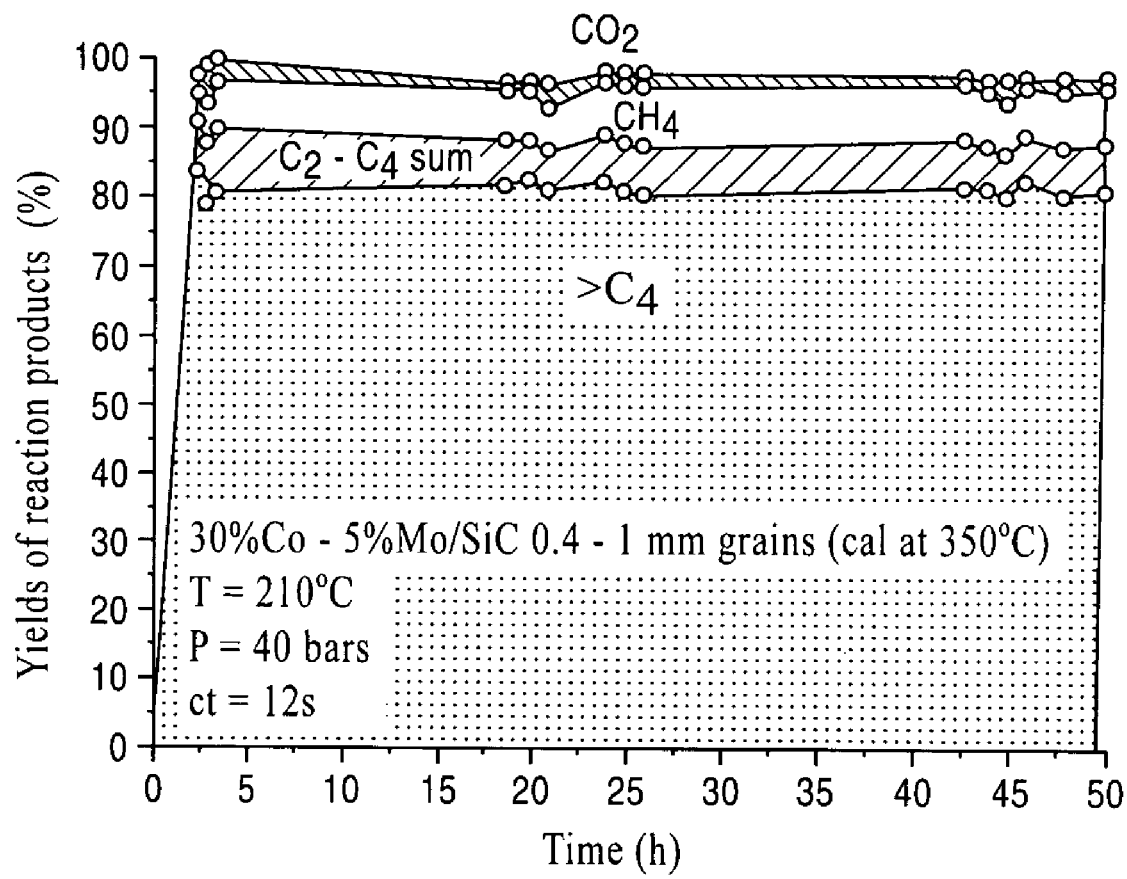

The results obtained at a reaction temperature of 200° C., expressed in terms of yield, are presented in FIG. 2A as a function of the time under flow. By comparison with those obtained in Example 1, it is found that the addition of molybdenum made it possible to increase, on the one hand, the stability of the activity and, on the other hand, substantially, the yield of liquid hydrocarbon at the expense of the light fractions, such as $CH_4$, $CO_2$ and $C_2$-$C_4$ hydrocarbons. In the presence of molybdenum, the distribution of the hydrocarbons in the liquid fraction is slightly shifted towards hydrocarbons with shorter chains, whereas the distribution of the olefinic/branched fractions remains unchanged. This emerges from FIG. 2B, which represents the distribution of the hydrocarbons within the liquid fraction ($C_4^+$).

The concentration of the olefinic and branched hydrocarbons likewise remains low (less than 1% on average).

EXAMPLE 3

Influence of the Reaction Temperature on the Activity in the Fischer-Tropsch Synthesis Over Catalysts Based on Co and on Co with Mo Promoter.

In this example, the support based on β-SiC is identical to that of Example 2.

The Fischer-Tropsch synthesis reaction is carried out under the following conditions:
  total pressure: 40 atmospheres
  reaction temperature: 200° C. and 210° C.
  reactants/catalyst contact time: 12 sec.

In the presence of molybdenum, the yield of the fraction comprising liquid hydrocarbons is always higher compared with that obtained in the absence of molybdenum on the catalyst, this being the case whatever the reaction temperature. The presence of molybdenum reduces the formation of the light products, such as $CO_2$ and $CH_4$, and promotes the formation of the liquid hydrocarbons, this being the case whatever the reaction temperature, i.e. 200° C. or 210° C. It should also be noted that, in the presence of molybdenum, the activity in the Fischer-Tropsch synthesis of the catalyst is more stable than in the absence of molybdenum.

The various results in terms of yields of the various fractions during the Fischer-Tropsch synthesis are given in FIGS. 1A, 2A, 3A and 3B.

EXAMPLE 4

Fischer-Tropsch Synthesis Over a Catalyst Based on Cobalt Supported on a β-SiC Monolith.

In this example, the support based on β-SiC, in the form of a monolith with a mean cell opening size of approximately 500 μm, is impregnated by the pore volume method with an aqueous solution comprising the cobalt salt in the nitrate form. The impregnation process is the same as in Example 1.

The Fischer-Tropsch synthesis reaction is carried out under the following conditions:
  total pressure: 40 atmospheres
  reaction temperature: 220° C.
  reactants/catalyst contact time: 12 sec.

Figure 4A:
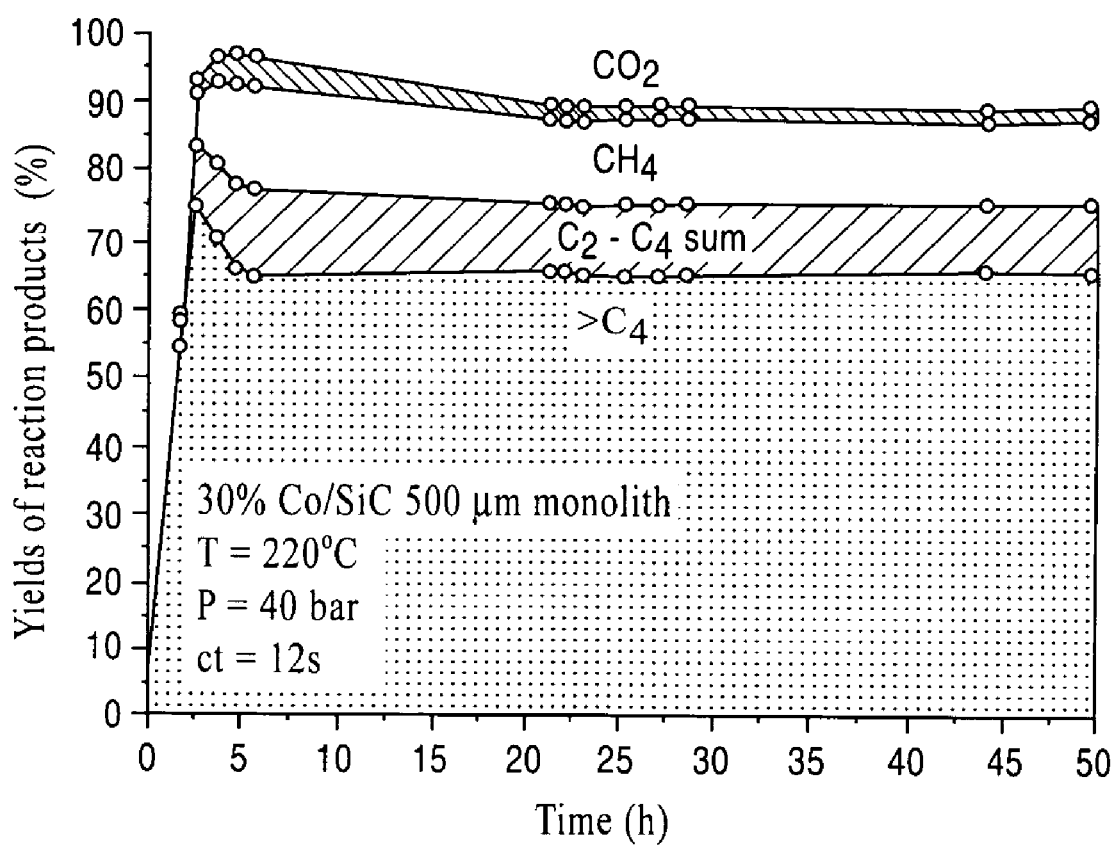
FIG. 4A gives the results of the yields of the various fractions as a function of the time under flow for a fifth embodiment.
Figure 4B:
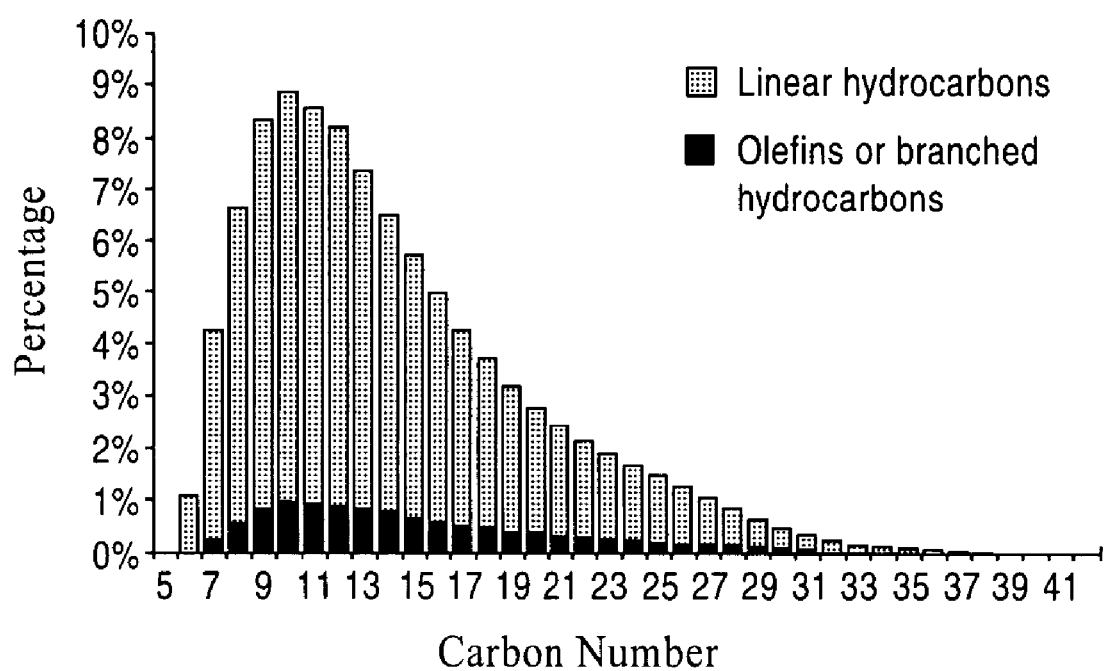
FIG. 4B gives the distribution of the hydrocarbons within the liquid fraction for this fifth embodiment.

The results obtained, expressed in terms of yields of the various fractions, are presented in FIG. 4A as a function of the time under flow. FIG. 4B gives the distribution of the hydrocarbons within the liquid fraction ($C_4^+$). The yield of liquid products remains high despite the reaction temperature of 220° C. This is attributed to the high thermal conductivity of the support based on β-SiC, which prevents hot spots and improves the selectivity. The results are of the same nature as those obtained in Example 1.

In the preceding examples, analysis at very high definition demonstrates unquantifiable $C_1$ to $C_{10}$ alcohols: the effluent is substantially devoid of alcohol.

The invention claimed is:

1. Process for the conversion of carbon monoxide to $C_2^+$ hydrocarbons in the presence of hydrogen and of a catalyst comprising a metal and a support, wherein the support consists of silicon carbide in the beta form.

2. Process according to claim 1, wherein the support of the catalyst comprises 100% by weight of beta silicon carbide in the particulate state.

3. Process according to claim 1, wherein the catalyst comprises at least 5% by weight of a metal selected from the group consisting of cobalt, iron and ruthenium.

4. Process according to claim 1 wherein the catalyst additionally comprises a promoter selected from the group consisting of Zr, K, Na, Mn, Sr, Cu, Cr, W, Re, Pt, Ir, Rh, Pd, Ru, Ta, V, Mo and their mixtures.

5. Process according to claim 1, wherein the catalyst additionally comprises a promoter which is Mo.

6. Process according to claim 1, wherein the beta-SiC is in the form of a powder, grains, extrudates, foam or monolith.

7. Process according to claim 1, wherein the catalyst is used as a fixed bed, as an ebullating bed or as a slurry.

8. Process according to claim 1, which is carried out under the following operating conditions:
  total pressure: 10 to 100 atmospheres;
  reaction temperature: 160 to 250° C.;
  GHSV varying from 150 to 5000 $h^{-1}$;
  $H_2/CO$ ratio of the starting synthesis gas of between 1.2 and 2.8.

9. Process according to claim 1, which is carried out under the following operating conditions:
  total pressure: 20 to 50 atmospheres;
  reaction temperature: 180 to 220° C.;
  GHSV varying from 200 to 1000 $h^{-1}$; $H_2/CO$ ratio of the starting synthesis gas of between 1.7 and 2.3.

10. Process according to claim 1 wherein the hydrocarbon effluent comprises more than 70 mol% of a mixture comprising from 50 to 90 mol% of $C_6$ to $C_{12}$ hydrocarbons and from 10 to 50 mol% of $C_{13}$ to $C_{24}$ hydrocarbons.

11. Process according to claim 1, wherein the hydrocarbon effluent comprises at most 10 mol% of branched hydrocarbons and olefins or less than 2 mol% of $C_1$ to $C_{20}$ alcohol or both.

12. Process according to claim 1, wherein, in the hydrocarbon effluent, the content of methane and of $CO_2$ is less than 20 mol%.

13. Process according to claim 1, wherein the hydrocarbon effluent comprises more than 70 mol% of a mixture comprising from 50 to 90 mol% of $C_6$ to $C_{12}$ hydrocarbons and from 10 to 50 mol% of $C_{13}$ to $C_{24}$ hydrocarbons.

14. Process according to claim 13, wherein the hydrocarbon effluent comprises at most 10 mol% of branched hydrocarbons and olefins or less than 2 mol% of $C_1$ to $C_{20}$ alcohol or both.

15. Process according to claim 13, wherein, in the 5 hydrocarbon effluent, the content of methane and of $CO_2$ is less than 20 mol%.

16. Process according to claim 13, carried out in a fixed bed.

17. Process according to claim 13, wherein the hydrocarbon effluent comprises more than 90 mol% of a $C_6$ to $C_{25}$ mixture.

18. Process according to claim 13, wherein the hydrocarbon effluent comprises levels of greater than 6% for the $C_7$, $C_8$, $C_9$, $C_{10}$, $C_{11}$, $C_{12}$ and $C_{13}$ hydrocarbons.

19. Process according to claim 13, wherein the hydrocarbon effluent comprises levels of greater than 8% for the $C_8$, $C_9$, $C_{10}$ and $C_{11}$ hydrocarbons.

20. Process according to claim 13, wherein the hydrocarbon effluent comprises a concentration of the olefinic hydrocarbons of less than 1%.

21. Process for the conversion of carbon monoxide to $C_2^+$ hydrocarbons in the presence of hydrogen and of a catalyst comprising a metal and a support wherein the support, consists of silicon carbide in the beta form, and wherein the hydrocarbon effluent comprises more than 70 mol% of a mixture comprising from 50 to 90 mol% of $C_6$ to $C_{12}$ hydrocarbons and from 10 to 50 mol% of $C_{13}$ to $C_{24}$ hydrocarbons.

22. Process according to claim 21, wherein the hydrocarbon effluent comprises at most 10 mol% of branched hydrocarbons and olefins or less than 2 mol% of $C_1$ to $C_{20}$ alcohol or both.

23. Process according to claim 21, wherein, in the hydrocarbon effluent, the content of methane and of $CO_2$ is less than 20 mol%.

24. Process according to claim 21, carried out in a fixed bed.

25. Process according to claim 21, wherein the hydrocarbon effluent comprises more than 90 mol% of a $C_6$ to $C_{25}$ mixture.

26. Process according to claim 21, wherein the hydrocarbon effluent comprises levels of greater than 6% for the $C_7$, $C_8$, $C_9$, $C_{10}$, $C_{11}$, $C_{12}$ and $C_{13}$ hydrocarbons.

27. Process according to claim 21, wherein the hydrocarbon effluent comprises levels of greater than 8% for the $C_8$, $C_9$, $C_{10}$ and $C_{11}$ hydrocarbons.

28. Process according to claim 21, wherein the hydrocarbon effluent comprises a concentration of the olefinic hydrocarbons of less than 1%.

\* \* \* \* \*